(12) United States Patent
Mazza et al.

(10) Patent No.: US 10,595,769 B2
(45) Date of Patent: Mar. 24, 2020

(54) ASPIRATION DEVICE AND METHOD FOR DETERMINING VISCOELASTIC PROPERTIES OF BIOLOGICAL TISSUES AND SYNTHETIC MATERIALS

(71) Applicant: ETH Zurich, Zurich (CH)

(72) Inventors: Edoardo Mazza, Wettingen (CH); Francisco Feijo Delgado, Zurich (CH); Clemens Clausen, Zurich (CH)

(73) Assignee: ETH Zurich, Zurich (CH)

( * ) Notice: Subject to any disclaimer, the term of this patent is extended or adjusted under 35 U.S.C. 154(b) by 0 days.

(21) Appl. No.: 16/347,312

(22) PCT Filed: Oct. 25, 2017

(86) PCT No.: PCT/EP2017/077236
§ 371 (c)(1),
(2) Date: May 3, 2019

(87) PCT Pub. No.: WO2018/082978
PCT Pub. Date: May 11, 2018

(65) Prior Publication Data
US 2019/0254587 A1 Aug. 22, 2019

(30) Foreign Application Priority Data
Nov. 4, 2016 (EP) .................... 16197195

(51) Int. Cl.
*A61B 5/00* (2006.01)
*G01L 13/00* (2006.01)
*G01L 13/02* (2006.01)

(52) U.S. Cl.
CPC ............ *A61B 5/442* (2013.01); *A61B 5/0055* (2013.01); *A61B 5/435* (2013.01); *G01L 13/02* (2013.01); *A61B 2562/0247* (2013.01)

(58) Field of Classification Search
CPC ... G01L 19/147; G01L 9/0042; G01L 9/0054; G01L 9/0072; G01L 13/025; G01L 19/04;
(Continued)

(56) References Cited

U.S. PATENT DOCUMENTS

| 4,976,272 A | 12/1990 | Bazin et al. |
| 5,535,676 A * | 7/1996 | Buschulte ............... B41F 23/06 101/416.1 |

(Continued)

FOREIGN PATENT DOCUMENTS

EP 0255809 A1 10/1988

OTHER PUBLICATIONS

Badir et al., "A Novel Procedure for the Mechanical Characterization of the Uterine Cervix During Pregnancy," Journal of the Mechanical Behavior of Biomedical Materials, 2013, pp. 143-153, vol. 27.

(Continued)

*Primary Examiner* — Andre J Allen
(74) *Attorney, Agent, or Firm* — The Webb Law Firm

(57) ABSTRACT

A device for measuring the elastic deformability of soft tissue has a probe head having the form of a cup with a cavity, side walls and a bottom wall, a first probe channel, a pressure unit and a control unit, the first probe channel being configured to connect the pressure unit, that provides a vacuum inside first probe channel and that is controlled by the control unit with the probe head. The first probe channel has a distal end leading through the bottom wall into the cavity. The device further has a second probe channel having a distal end leading through the bottom wall into the cavity and being connected with a pressure sensor provided to determine the pressure in the cavity and to communicate it to the control unit to determine a point in time, when deformed tissue closes the distal end of the first probe (Continued)

channel based on a pressure difference in the two probe channels.

17 Claims, 12 Drawing Sheets

(58) Field of Classification Search
CPC . G01L 19/0038; G01L 19/0084; G01L 19/14; G01L 9/0075; G01L 19/0069; G01L 19/0618; G01L 9/0055; G01L 9/0073; G01L 19/0092; G01L 19/0645; G01L 19/143; G01L 9/0051; G01L 9/0052; G01L 11/025; G01L 19/0007; G01L 19/0046; G01L 19/06; G01L 19/0627; G01L 19/0681; G01L 27/002; G01L 9/00; G01L 9/0041; G01L 9/0044; G01L 11/04; G01L 19/0023; G01L 19/069; G01L 19/142; G01L 19/16; G01L 7/00; G01L 7/163; G01L 7/166; G01L 9/0047; G01L 9/12; G01L 11/02; G01L 13/00; G01L 15/00; G01L 19/003; G01L 19/0609; G01L 19/0672; G01L 19/083; G01L 19/10; G01L 19/148; G01L 27/005; G01L 7/08; G01L 7/082; G01L 9/0045; G01L 9/0048; G01L 9/006; G01L 9/007; G01L 9/0076; G01L 9/04; G01L 9/045; G01L 9/06; G01L 9/065; G01L 9/125; G01L 11/00; G01L 17/00; G01L 19/00; G01L 19/0015; G01L 19/0076; G01L 19/02; G01L 19/08; G01L 19/141; G01L 19/145; G01L 19/146; G01L 1/142; G01L 1/2262; G01L 1/246; G01L 21/12; G01L 23/16; G01L 27/007; G01L 7/04; G01L 7/063; G01L 7/084; G01L 7/086; G01L 7/16; G01L 9/0002; G01L 9/0007; G01L 9/0016; G01L 9/0019; G01L 9/0022; G01L 9/0027; G01L 9/0033; G01L 9/0039; G01L 9/005; G01L 9/0058; G01L 9/0077; G01L 9/0079; G01L 9/008; G01L 9/0092; G01L 9/0095; G01L 9/025; G01L 9/08; G01L 9/085; G01L 9/105; G01L 9/14; G01L 9/16; A61B 2017/22079; A61B 17/221; A61B 17/22; A61B 2090/3966; A61B 10/0283; A61B 17/3403; A61B 2010/045; A61B 2017/00778; A61B 2017/00867; A61B 2017/2215; A61B 2217/005; A61B 10/0233; A61B 10/0275; A61B 17/22031; A61B 17/32002; A61B 17/320068; A61B 17/32053; A61B 17/34; A61B 1/2676; A61B 2010/0208; A61B 2017/00358; A61B 2017/00752; A61B 2017/00862; A61B 2017/22038; A61B 2017/22051; A61B 2017/22067; A61B 2017/306; A61B 2017/3435; A61B 2017/3454; A61B 2090/064; A61B 34/30; A61B 5/154; A61B 10/0045; A61B 10/0096; A61B 10/025; A61B 10/0266; A61B 10/04; A61B 17/00234; A61B 17/0642; A61B 17/12036; A61B 17/12104; A61B 17/12109; A61B 17/1214; A61B 17/12168; A61B 17/12172; A61B 17/22032; A61B 17/24; A61B 17/32037; A61B 17/32056; A61B 17/320725; A61B 17/322; A61B 17/3417; A61B 17/3421; A61B 17/3439; A61B 17/3478; A61B 17/562; A61B 17/8816; A61B 17/8822; A61B 17/8825; A61B 17/8833; A61B 18/1477; A61B 18/1492; A61B 1/00009; A61B 1/00045; A61B 1/00055; A61B 1/00066; A61B 1/00096; A61B 1/00098; A61B 1/00103; A61B 1/00133; A61B 1/00163; A61B 1/0051; A61B 1/0058; A61B 1/018; A61B 1/041; A61B 1/042; A61B 1/05; A61B 1/051; A61B 1/273; A61B 1/313; A61B 1/3132; A61B 1/317; A61B 2010/0216; A61B 2010/0225; A61B 2010/0258; A61B 2017/00022; A61B 2017/00146; A61B 2017/0023; A61B 2017/00292; A61B 2017/00398; A61B 2017/00792; A61B 2017/00809; A61B 2017/1205; A61B 2017/22034; A61B 2017/22039; A61B 2017/22044; A61B 2017/22054; A61B 2017/22061; A61B 2017/22084; A61B 2017/2212; A61B 2017/320024; A61B 2017/320044; A61B 2017/32006; A61B 2017/320064; A61B 2017/32007; A61B 2017/320075; A61B 2017/320078; A61B 2017/3225; A61B 2017/3407; A61B 2017/3411; A61B 2017/561; A61B 2017/8838; A61B 2018/00327; A61B 2018/00595; A61B 2034/2051; A61B 2034/302; A61B 2090/062; A61B 2090/3987; A61B 2217/007; A61B 2218/002; A61B 2218/007; A61B 2562/0247; A61B 2562/0295; A61B 34/71; A61B 5/0084; A61B 5/08; A61B 5/1411; A61B 5/1438; A61B 5/14514; A61B 5/14532; A61B 5/14539; A61B 5/14546; A61B 5/1455; A61B 5/1486; A61B 5/150022; A61B 5/150099; A61B 5/150206; A61B 5/150213; A61B 5/150221; A61B 5/150229; A61B 5/150343; A61B 5/150358; A61B 5/150412; A61B 5/150419; A61B 5/150503; A61B 5/150755; A61B 5/150969; A61B 5/150984; A61B 5/151; A61B 5/15105; A61B 5/15142; A61B 5/42; A61B 5/4839; A61B 5/4842; A61B 5/6852; A61B 5/6861; A61B 90/00; A61B 90/39; A61B 90/92
USPC .................................................. 73/700–756
See application file for complete search history.

(56) References Cited

U.S. PATENT DOCUMENTS

| 6,102,895 | A | * | 8/2000 | Cortella | ............. | A61M 1/0068 |
| | | | | | | 604/187 |
| 7,955,278 | B1 | | 6/2011 | Sarvazyan | | |
| 2011/0130683 | A1 | | 6/2011 | Sarvazyan | | |
| 2018/0133400 | A1 | * | 5/2018 | Almoumen | ............. | A61M 5/20 |

OTHER PUBLICATIONS

Schiavone et al., "In Vivo Measurement of Human Brain Elasticity Using a Light Aspiration Device," Medical Image Analysis, 2009, pp. 673-678, vol. 13.

(56) References Cited

OTHER PUBLICATIONS

Schiavone et al., "Lastic: A Light Aspiration Device for In Vivo Soft Tissue Characterization," Biomedical Simulation: 5th International Symposium, 2010, pp. 1-10, vol. 5958.

* cited by examiner

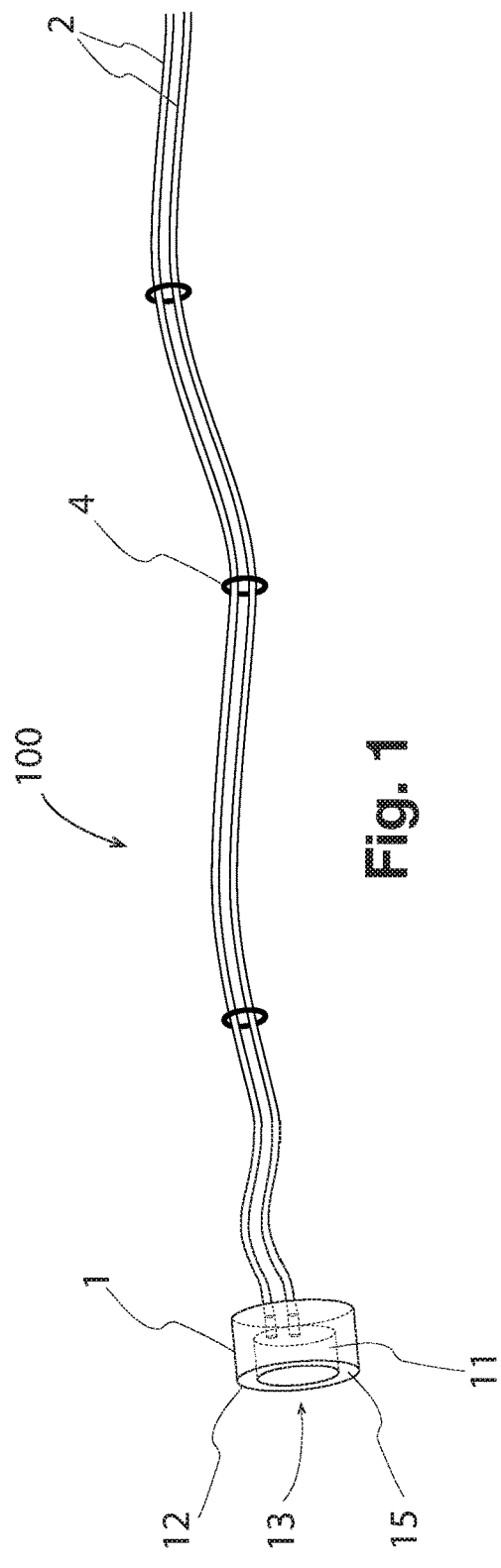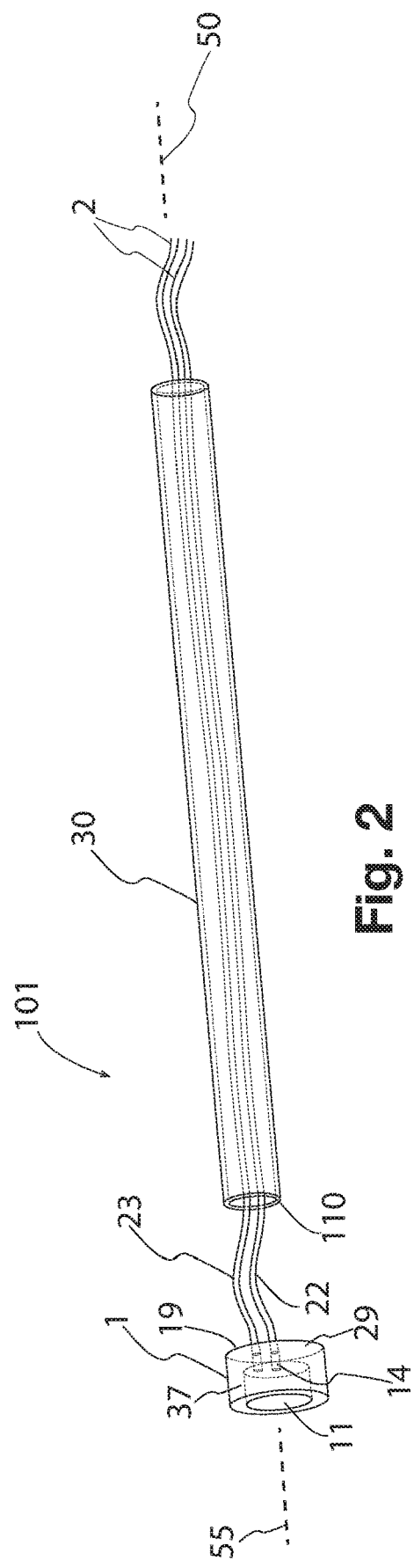

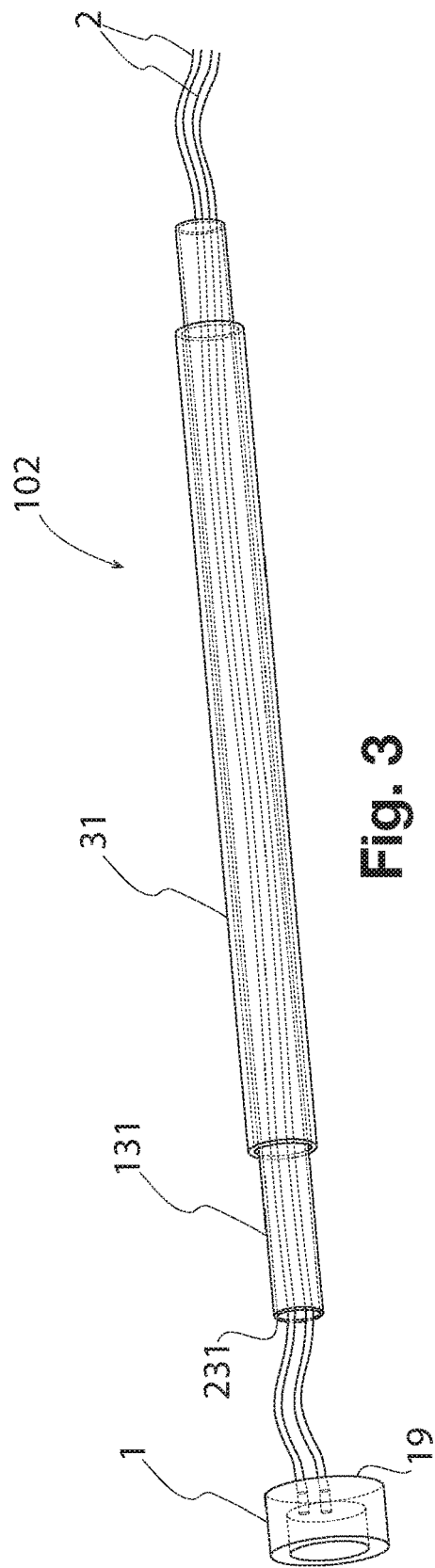
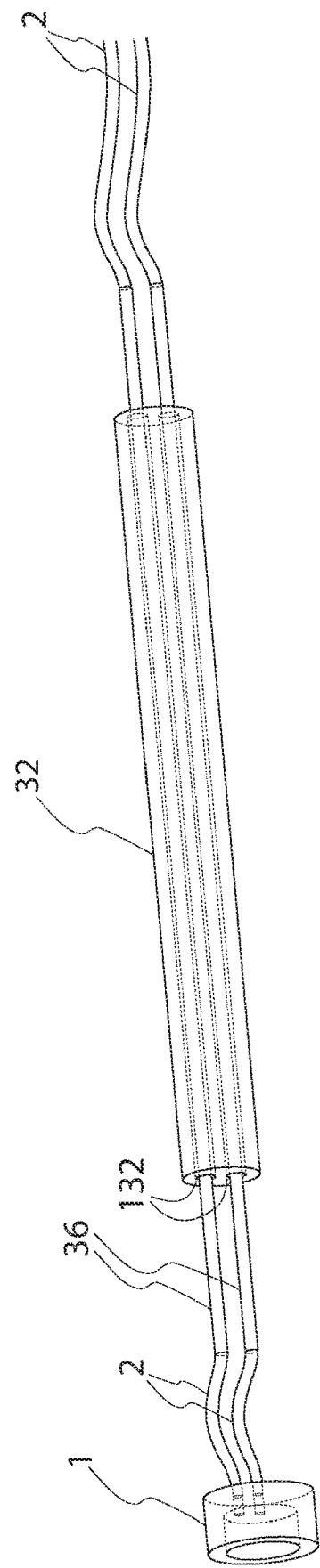

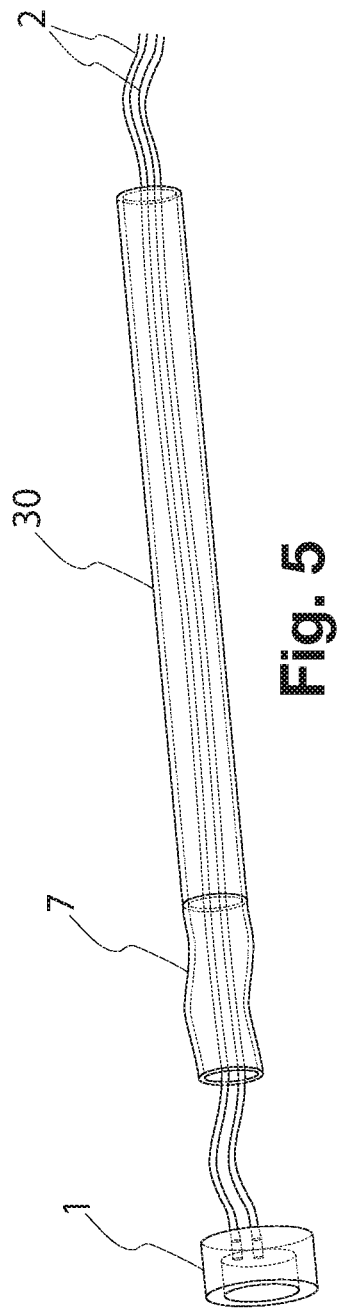
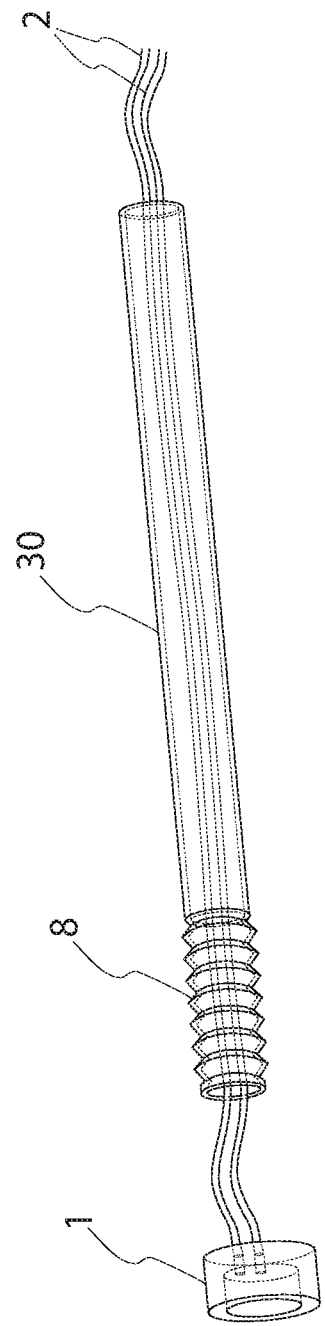

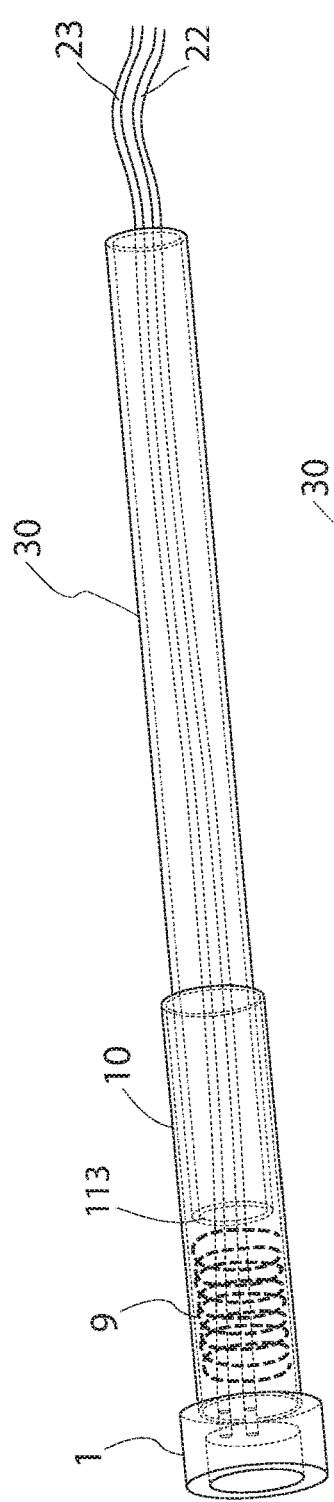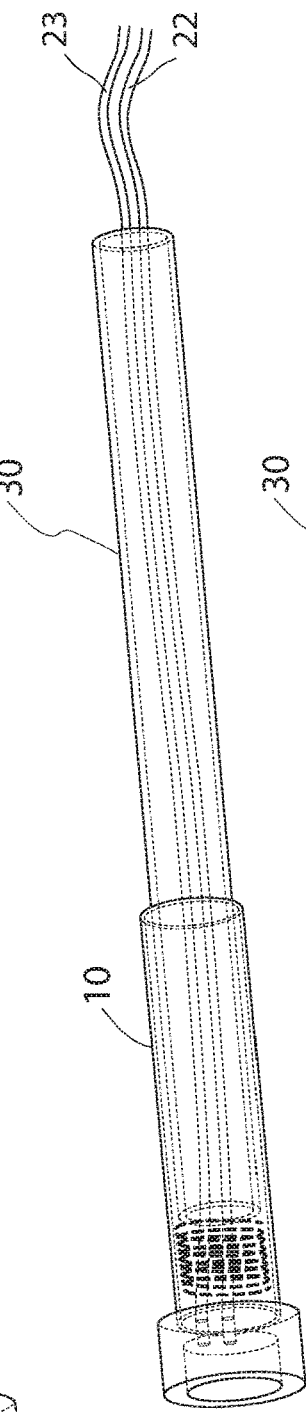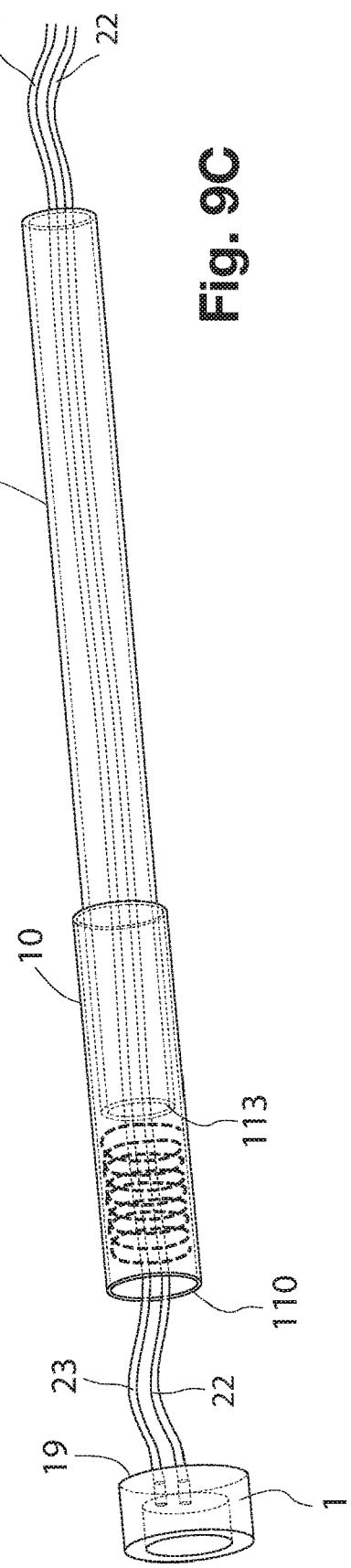

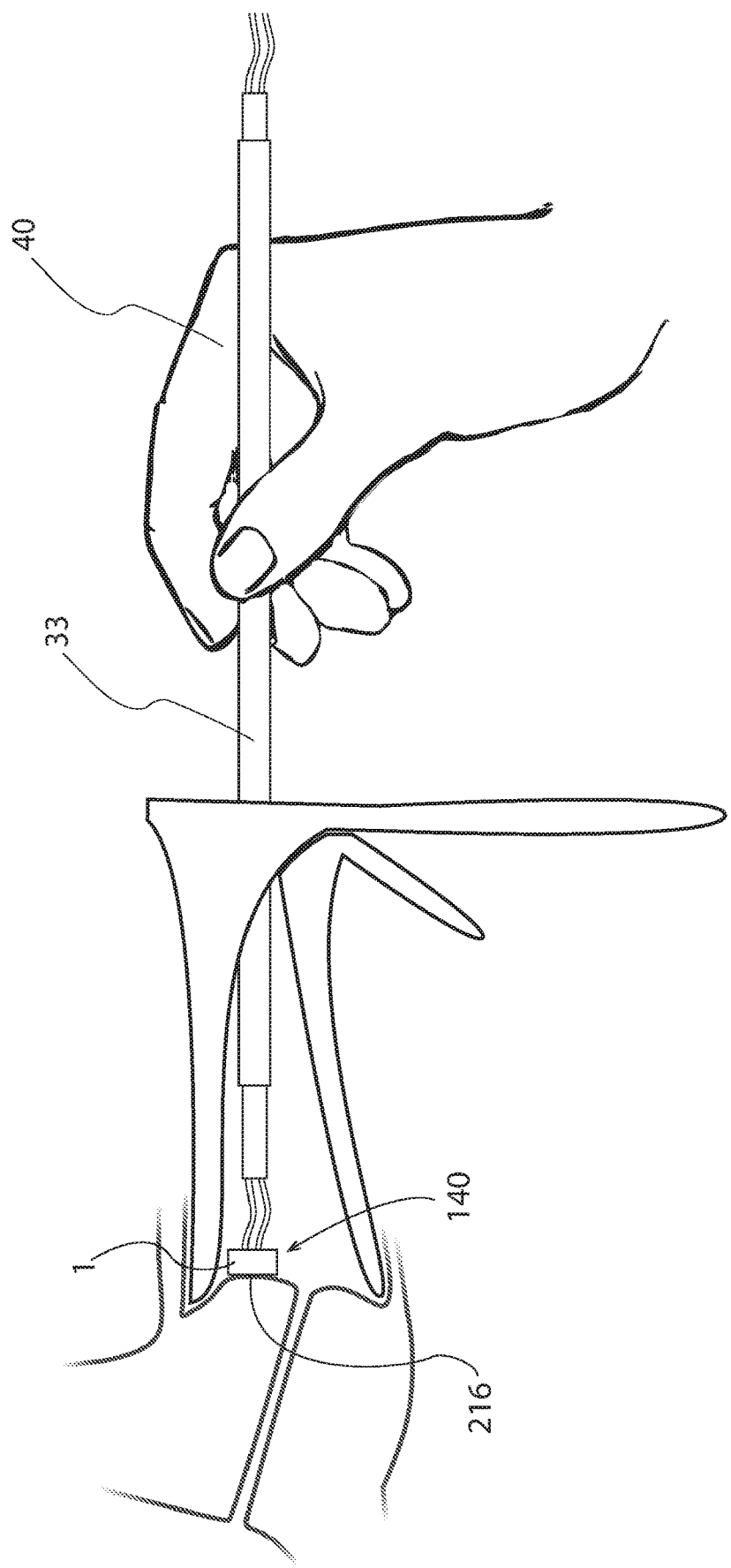

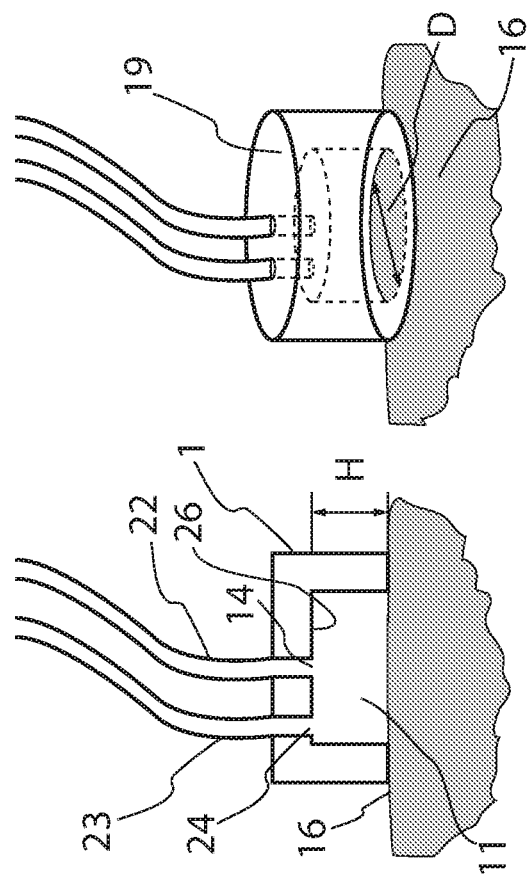
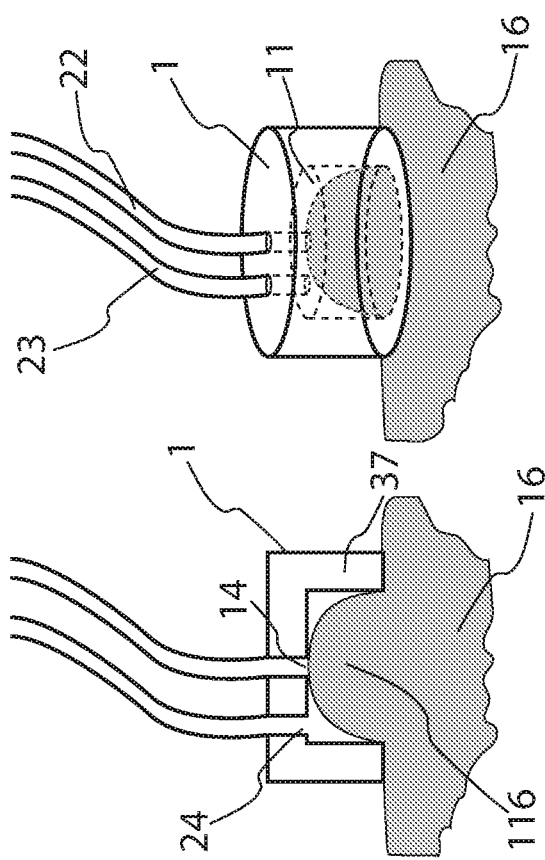
Fig. 12A
Fig. 12B

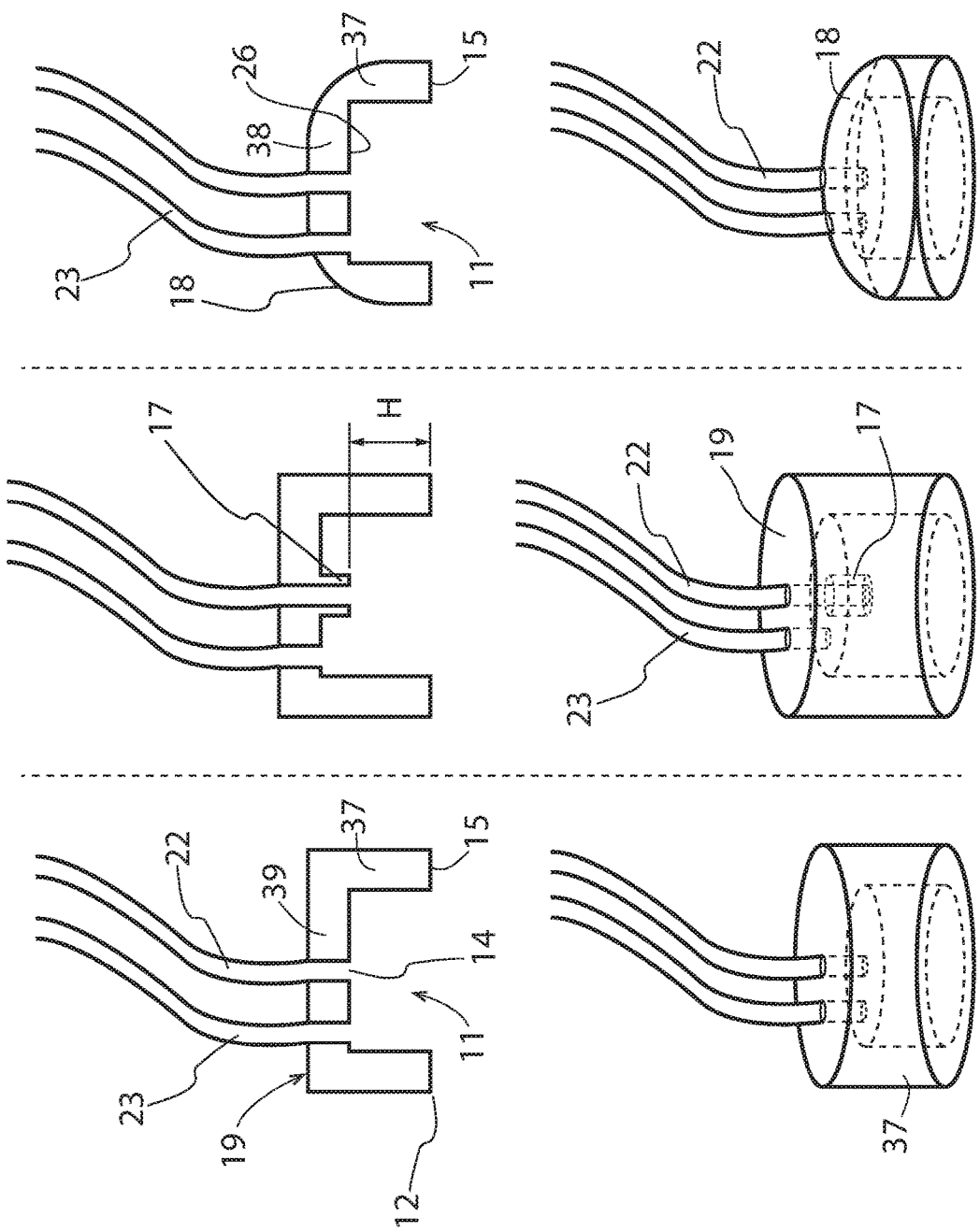

ASPIRATION DEVICE AND METHOD FOR DETERMINING VISCOELASTIC PROPERTIES OF BIOLOGICAL TISSUES AND SYNTHETIC MATERIALS

CROSS-REFERENCE TO RELATED APPLICATIONS

This application is the United States national phase of International Application No. PCT/EP2017/077236 filed Oct. 25, 2017, and claims priority to European Patent Application No. 16 197 195.7 filed Nov. 4, 2016, the disclosures of which are hereby incorporated by reference in their entirety.

BACKGROUND OF THE INVENTION

Field of the Invention

The present invention relates to an aspiration device and method for determining elastic and/or viscoelastic properties of soft and very soft tissues, biological tissues and synthetic materials.

Description of Related Art

A common way of measuring mechanical properties of biological tissues relies on the aspiration of the test tissue, usually with a probe that has a cavity, inside which a negative pressure is generated. This causes the tissue surface to be displaced and a certain volume of tissue to deform into this cavity. The mechanical properties can be determined by analysing the displacement for a set pressure value, or by analysing the required pressure to obtain a set displacement condition.

Schiavone P, F. Chassat, T. Boudou, E. Promayon, F. Valdivia, Y. Payan describe in "In vivo measurement of human brain elasticity using a light aspiration device Medical Image" in Analysis 13 (2009) 673-678, a lightweight aspirator for in vivo measurement of soft tissues. An update was published by Schiavone P, Promayon E, Payan Y. with "LASTIC: a light aspiration device for in vivo soft tissue characterization" in Lecture Notes in Computer Science 5958 (2010) p. 1-10. While designed for in vivo measurements and to withstand sterilization, this device is only practical to be used in exposed tissues, too heavy for very soft tissues and still too bulky for intra-corporal tissue measurements. Furthermore, it measures displacement through a camera incorporated into the probe head, which raises the device complexity and cost, making it impractical for the development of a disposable instrument.

Badir, S., Bajka, M., Mazza, E. have published "A novel procedure for the mechanical characterization of the uterine cervix during pregnancy." in J Mech Behav Biomed Mater, 27 (2013) 143-153 relating to a cervical aspirator that uses a fixed tissue displacement distance and measures the negative pressure required to achieve such displacement. This negative pressure is detected by a differential measurement that occurs when the displaced tissue seals an internal pipe and the pressures inside and outside the internal pipe are measured by two sensors in a remote control unit. While achieving high pressure sensitivity detection in a small cross-section aspirator probe that can easily be used in intra-corporally, it requires an endoscope to allow the correct positioning of the device as well as to give feedback to the user on when the contact between the probe and the sensor occurs.

EP 0 255 809 relates to a device for the measurement of the elasticity of the human skin having a suction cup in which negative pressure is applied, in order to deform the tissue. Later, the pressure is returned to zero, and a volume of displaced air is measured inside a syringe, corresponding to the remaining deformation displayed by the skin. The setup is simple, but the system presents severe limitations regarding the accuracy of measured volume and requires perfect tightness of the whole system. The suction means of the system represents a commercial syringe as a plunger-type suction means provided with a graduated scale. Someone skilled in the art refers such syringes to a volume between 1 and 100 milliliter. Therefore, the accuracy of a measurement with such an instrument can be at the most between 0.1 and 10 milliliter skin deformation, depending on the syringe size and the tightness of the system. The user has to ensure that the sealing contact is achieved before the actuation of the syringe takes place. The system according to EP 0 255 809 809 mentions that a negative pressure of 10 mmHg is to be reached in the sucking phase and then the negative pressure is decreased until the pressure gauge shows a zero value to evaluate the deformation of the skin through reading the graduated scale of the syringe.

U.S. Pat. No. 7,955,278 discloses aspiration methods and devices for assessment of viscoelastic properties of soft tissues, wherein the device uses a fixed tissue displacement distance and measures the negative pressure required to achieve such displacement. Aspiration is done through one opening of the cavity, and the required negative pressure value to achieve the displacement is detected by a change in the of rate aspiration, due to a significant change in aspiration volume: when the displaced tissue seals an internal aspiration pipe, a significant change in volume is created as the main volume of the chamber is isolated from the pump. Thus, the evacuation volume is significantly reduced leading to a discontinuity in the rate of increase of the negative pressure as the pumping continues. This method requires that a cavity large enough exists, in order to provide a significant ratio of volumes between the cavity and the internal pipe, so that a small error is obtained (the ratio is indicated to range between 2 to 10). While the tip of the probe can be miniaturized, this still leads to an overall bulky probe head.

U.S. Pat. No. 4,976,272 is related to a method and device for measuring the elasticity of a superficial layer, in particular of the skin, wherein the device uses a fixed tissue displacement distance and measures the negative pressure required to achieve such displacement. The pressure change is monitored inside the cavity, through one aperture, and the change stops at the moment that the tissue closes another aperture, from which the cavity air is being evacuated, and that is located at a certain distance from the aperture opening. The solution presented, however, requires a large internal air chamber, for reasons of pressure measurement stability that makes the probe large and bulky.

SUMMARY OF THE INVENTION

Based on this prior art, it is an object of the invention to overcome the limitations of prior art by providing novel devices and methods for the quantitative evaluation of the viscoelastic properties of soft and very soft biological tissues and synthetic materials.

An important requirement for a reliable measurement is the establishment of a non-perturbed initial condition of the tissue under analysis. This means that the tissue should not be compressed or deformed due to any external force other than the negative pressure generated inside the analysis suction cavity. In particular, when measuring soft biological tissues two factors that may unwantedly perturb the resting state of the tissue are: 1) the influence of the user-generated contact forces while positioning and holding the instrument on the tissue and 2) involuntary movements of the test subject that change the relative position between the tissue and the measuring probe.

These factors affect, in particular, the reliability of measurements of longer duration, such as for slow negative pressure application, or for tests involving several loading cycles. This strongly limits the possibility to characterize the time-dependent behaviour of tissues, i.e. their viscoelastic properties.

Very soft tissues are highly deformable and, therefore, the overall user-generated contact force should be minimal—essentially zero—throughout the measurement. Furthermore, if such measurement is to take place at a non-exposed surface, there should be a way to place the suction probe at this internal surface, while maintaining the above mentioned minimal contact force requirements. In addition, certain tissues or body locations may require the device to be sterile, therefore a measurement system compatible with various sterilization methods is a necessity. Finally, to allow a successful usage of such device in a medical context, an apparatus providing the above describe functionalities should not possess excessive mechanical and usability complexity, in order to prevent high costs, low precision or the requirement of highly skilled operators.

The present invention provides technical solution for a device together with a measurement system for the measuring of the mechanical properties of soft and very soft biological tissues or synthetic materials, having a simple mechanism, low cost, being safe and easy to operate, while being capable of providing a precise, accurate and reproducible characterization of the viscoelastic properties of materials.

A device for measuring the elastic deformability of soft tissue comprises a probe head having the form of a cup with a cavity, side walls and a bottom wall, a first probe channel, a pressure unit and a control unit, the first probe channel being configured to connect the pressure unit, that provides a vacuum inside first probe channel and that is controlled by the control unit, with the probe head, wherein the first probe channel has a distal end leading through the bottom wall into the cavity and extends optionally at least partly into the cavity. The device comprises a second probe channel having a distal end leading through the bottom wall into the cavity and being connected with a pressure sensor provided to determine the pressure in the cavity and to communicate it to the control unit to determine the point in time, when deformed tissue closes the distal end of the first probe channel based on a pressure difference in the two probe channels, wherein the two probe channels are flexible tubes passing loosely through a hollow sleeve allowing an essentially free relative movement between probe head and hollow sleeve.

The front edge of the sleeve is configured, in an embodiment of the invention, to support the bottom wall of the probe head enabling a user to move the probe head and the sleeve as a single unit. There, it might be interesting when the bottom wall of the probe head has a rounded proximal outer surface to orient the longitudinal axis of the probe head not parallel, i.e. obliquely, to the longitudinal axis of the sleeve The loosely inserted tubes can be used as Bowden cables to provide the orientation of the longitudinal axis of the probe head towards the longitudinal axis of the sleeve.

A dampening element can be fixedly attached at the front end of the sleeve. Such a dampening element can be a hollow elastomer or a bellows.

A bush can be provided encompassing or inserted into the sleeve, wherein the inner diameter of the outer bush or sleeve and the outer diameter of the inner sleeve or bush are chosen to accommodate one in the other under a slight frictional contact.

The dampening element can comprise a combination of a bush and a spring, wherein the spring is fixedly attached or abuts against an end wall of one of the sleeve or bush and is fixedly attached or abuts against the complementary connected shoulder of the other bush or sleeve.

The probe head can have a cavity with a volume measured until the front surface between 0.78 microliter and 4 milliliter, preferably between 6 microliter and 3.5 milliliter, preferred between 0.1 and 1 milliliter. The dimensions of diameter or length or width, respectively and height are predetermined that the aspect ratio of the probe head is between 1/4 and 2 and more preferred between 1/2 and 1.

The thickness of the walls of the probe head are between 0.3 and 2 millimeter, so that the probe head is made of a plastic material and that the weight of the probe head is less than 2 grams and more preferred less than 1 gram.

The probe head is essentially in the form of a hollow cylinder and can have an additional closed internal cavity for vacuum clamping and comprises at least one recess in the area of its distal end, preferably 4 to 16 recesses, the at least one recess being in connection to the pressure unit, via a third probe channel, wherein optionally the at least one recess is provided on an inclined wall portion of the inner side of the probe head.

A method for measuring the elastic deformability of soft tissue by applying an under pressure on the soft tissue with a probe head is provided comprising the steps of:
  optionally, placing the probe head in an initial position on the front edge of the sleeve;
  moving the sleeve and the probe head, loosely connected via tubes or positioned on the front edge of the sleeve;
  applying the under pressure at least at some time before contact of the probe head with the tissue is made
  displacing the sleeve along the longitudinal direction until the distal end of the probe head contacts the soft tissue and a holding under pressure is reached in the cavity,
  retracting the sleeve along the longitudinal direction, while continuing to apply the holding under pressure or increasing the under pressure monotonically,
  increasing the under pressure monotonically until a sensor unit detects a difference in pressure between the two tubes, signaling the closure of a distal end,
  interrupting the under pressure once one distal end of the probe channel is closed, wherein the deformability of the soft tissue is measured as a pressure difference between the initial position and the final position After the initial cycle as mentioned above, a number of further cycles can follow comprising:
  reducing the under pressure to a value at or slightly larger than the holding under pressure,
  optionally applying said under pressure for predetermined intermediate time,
  increasing the under pressure monotonically until a sensor unit detects a difference in pressure between the two tubes, signaling a renewed closure of a distal end (14, 24), and interrupting the under pressure once one distal end of the probe channel is closed, wherein the deformability of the soft tissue) is measured as a pressure difference between the initial position and the final position.

Subsequent cycles may have different increase rate of the under pressure, i.e. becoming slower or faster or in a predetermined pattern.

The probe head can be a cylindrical cavity with a diameter between 1 and 20 millimeter, preferably between 6 and 16 millimeter and the height of the cavity can be between 1 and 10 millimeter, preferably between 2 and 6 millimeter. Preferably, the dimensions of diameter and height are chosen in a way that the aspect ratio is between 1/4 and 2 and more preferred between 1/2 and 1. If the cylinder has e.g. a square base, than the length of the sides of the square are about 0.78 times of the above mentioned values. This leads to volumes of the cavity between 0.785 microliter and 20 ml.

The probe head has a wall thickness of between 0.5 and 3 millimeter providing sufficient stiffness but is at the same time light weight.

The invention provides an ultralight aspiration device for determining elastic and/or viscoelastic properties of soft and very soft tissues with high precision and low variability. The tissues can be biological tissues or synthetic materials.

The specific advantages of the new system enable applications for mechanical characterization of soft and very soft biological tissues (e.g. cervix, skin, abdominal organs, cardiovascular tissues, brain), highly compliant elastomers or other synthetic materials, hydrogels, tissue engineering scaffolds, decellularized extracellular matrix, cellulose based materials or soft implants. One of the advantages of this system is the fact that it can provide a reliable characterization of viscoelastic properties in situ, i.e., without the need for extraction of material samples for mechanical testing.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 shows a perspective view of a device according to an embodiment of the invention;

FIG. 2 shows a perspective view of the device according to FIG. 1 with an applicator;

FIG. 3 shows a perspective view of the device according to FIG. 1 inside a double sleeve applicator;

FIG. 4 shows a perspective view of the device according to FIG. 1 inside an alternative multi-sleeve applicator;

FIG. 5 shows a perspective view of a device according to FIG. 2 with a modified applicator with dampening element;

FIG. 6 shows a perspective view of the device according to FIG. 2 with a modified applicator with a bellows bumper;

FIGS. 9A, 9B & 9C shows perspective views of a device according to FIG. 8 in different use positions;

FIG. 10 shows a schematic view of an application measuring the mechanical properties of a biological tissue inside a body cavity such as the uterine cervix;

FIGS. 12A & 12B shows cross-section and perspective views of a probe head as shown in FIG. 1;

FIGS. 13A, 13B & 13C show different configurations of probe heads usable in connection and within an embodiment of the invention;

DESCRIPTION OF PREFERRED EMBODIMENTS

Figure 7:
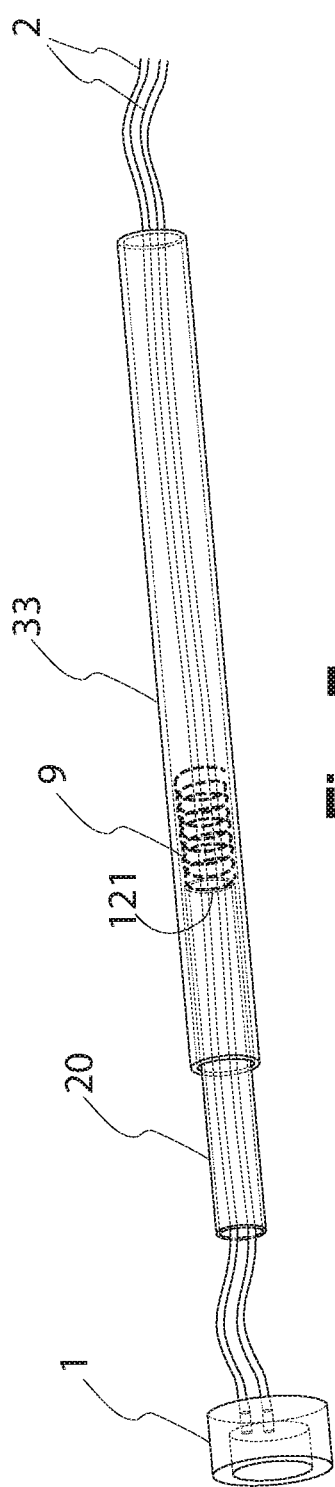
FIG. 7 shows a perspective view of a device similar to FIG. 3 with a coil based damper.

A device 100 for measuring the elastic deformability of soft tissue according to the present invention is shown in FIG. 1 providing a perspective partial cross section view of a lightweight probe head 1 of a device 100 according to an embodiment of the invention. FIG. 1 is described in connection with FIG. 12A and FIG. 12B showing each a cross-section and perspective view of a probe head 1 as shown in FIG. 1 before the actual suction starts (in FIG. 12A) and when one measuring cycle ends (in FIG. 12B), respectively.

Such probe head 1 can house a cylindrical cavity 11, for instance of D=8 mm diameter and height H=4 mm. The outer rim 12 diameter of 2 mm results in a cylindrical shaped probe of total diameter of 12 mm. Then the full volume of the solid portions of the probe head (including the tubes volume inside the upper wall 38, 39 of the probe head) is 477 $mm^3$ or 486 $mm^3$ with a wall thickness of 0.3 mm. The volumetric mass density of e.g. plastic material is generally between 0.8 and 2.2 g/cm3. Thus such a probe head weighs between 0.4 and 1 gram. Such probe head 1 can be created of lightweight, sterilizable materials as Polyether ether ketone (PEEK) or Polycarbonate (PC) and the total weight can be lower than 2 grams and even lower than 1 gram. This represents a considerable reduction of the weight and size of the probes of an order of magnitude compared to prior art.

Such probe head 1 has a front opening 13 surrounded by a circular flat bottom edge 15 and on the other side of the cavity 11 two openings 14 and 24, connected to two highly flexible and lightweight tubes 2 (in FIG. 1) that on the other end connect to a remote control unit (not shown) where a pump and pressure sensors are located.

The tubes 2 have received the reference numerals 22 and 23 depending on their function. The pump is connected to airway 22 and both airways 22 and 23 are terminated with a pressure sensor (not shown, measured pressure values shown as P1 and P2 in FIGS. 15 and 16). The pumping airway terminates at the opening or aperture 14 centrally located on the top inner surface 26 of the cavity 11. The other opening or aperture 24 of the second airway 23 can be placed anywhere inside the cavity, providing it is not blocked by the moving tissue. It is positioned in a radial distance from the central aperture 14 on the top inner surface 26.

The pump is adapted to provide a negative pressure of at least 100 mbar (75 mmHg), preferably being adapted to work in the range between 250 mbar (187 mmHg) to e.g. 750 mbar (562 mmHg), preferredly to reach a negative pressure level of at least 500 mbar (375 mmHg).

When the tissue 16 sealingly contacts the probe, a closed volume of air is defined (being the volume of the cavity 11 plus the volume of the tubes 2 until a valve or a sensor, and as this air is evacuated, the negative pressure generated inside this volume causes the tissue to be deformed into the cavity, until it touches the central aperture. At this instant, as depicted in FIG. 12b, the tissue 16 will sealingly contact the airway 22 aperture 14. At this moment, as previously described by Badir and colleagues (see prior art citation), the pressure sensors measure distinct pressures, allowing for a precise determination of the closing pressure, or pressure required for the displacement H. Such measurement method does not rely on the change of aspiration rates, thus discarding the need for a significant change in volume as described by U.S. Pat. No. 7,955,278 B1, allowing for an overall small probe head 1.

Furthermore, the detection of an inflection point due to change in aspiration rate, can be practically challenging due to discrete measurements by the sensors and uncertainty caused by measurement noise, while distinguishing two different pressures is more easily implemented with a differential threshold. In addition, such method does not rely on the imposition of strictly linear aspiration curves.

A small and very light probe head overcomes limitations of prior art by having a minimal weight applied to the tissue under analysis, guaranteeing that minimal pre-deformation of the tissue occurs, as well as having a small contact area footprint, as large as necessary to avoid slippage, easily allowing to be inserted into body cavities or other apertures. In addition, with the differential measurement procedure, this system leads to higher precision measurements, owing to the minimal influence on the tissue and the accurate determination of the necessary stress for a given displacement.

The airways 2, or 22, 23, respectively are highly be flexible, allowing for an unconstrained and unrestricted placement of the probe head 1. This guarantees that almost no external forces are transmitted through the connections so that the only external force affecting the measurement is the extremely low weight of the probe head 1.

Before the placement of the probe head 1, suction is initiated, allowing for the detection of sealing contact, when negative pressures are detected at the sensors. After a few seconds, the negative pressure is enough to hold the probe head 1 sealingly attached to the tissue surface 16, without the need for an external force. The flexible airways 2 can be mechanically supported, in order to further minimize any transmission of forces, avoiding a rigid mechanic connection between the probe user and the tissue 16. The probe self-adheres to the tissue 16 and movements of the user are no longer transmitted to the tissue. Furthermore, as tissue 16 and probe head 1 are mutually joined, any movements of the tissue 16 are accompanied by the probe head 1 (e.g. the involuntary movements of the measurement subject).

As explained above, such setting limits the forces between probe head 1 and tissue 16 to the weight of probe head 1. The effect of this force depends on the relative orientation of the system relative to gravity. This will result in compressive forces, tensile forces, or a combination, as a torsional or bending force. To achieve minimal forces, the probe head 1 is, as previously described, ultra-light (<2 g) and with a low aspect ratio in order to minimize loads when the probe head 1 is applied laterally. The aspect ratio in the example described above is a diameter of 12 mm and a height of 8 mm. The aspect ratio is 2/3. It is usually chosen to be below 2 and preferredly below 1. A lower threshold value, although not necessarily connected is 1/4 or 1/2. Therefore, a preferred aspect ratio is situated between 1/4 and 2 and more preferred between 1/2 and 1.

FIG. 13A, FIG. 13b and FIG. 13C show different configurations of probe heads usable in connection and within an embodiment of the invention. The upper drawings show a cross section view, whereas the lower drawings show a partial cross section perspective view. A planar top inner surface 26 of the cavity 11 as depicted in FIG. 13A and FIG. 13C does not expose the displaced tissue 116 (see FIG. 12B) to any sharp edges, however, the geometry of the inner cavity can be adapted to different usage needs or aspiration safety requirements. For instance, the probe head 1 can also present a protruding central stem 17 on top inner surface 26 of the cavity 11 as depicted in FIG. 13B in order to prevent tissue 16 with irregular topography to contact the top inner surface of the cavity before sealingly closing the airway. The probe head 1 can be shaped in multiple ways in order to reduce the total construction material, thus weight and costs and improve the aspect ratio, as exemplified with the dome-shaped probe head 18 in FIG. 13C. The aspect ratio of the three embodiments are 6/13, 5/9 and 4/9. The height for the aspect ratio is measured between the bottom edge 15 and the upper surface 19 where the flexible tubes 22, 23 are entering, preferredly in one piece into the probe head 1.

Here, it can also be that the probe head 1 has protruding sockets, into which the tubes are affixed (similar to the stem 17, but the sockets are coming upwards from surface 19 towards the outside). Then the upper wall 38 or 39 of the probe head have through holes ending in said sockets.

The width of the aspect ratio is measured as the diameter of the ring shaped rim 12. For a rectangular probe head basis, the width is defined as the average width of the probe head basis with the proviso that one dimension is not to be more than twice as long as the other dimension, which is automatically achieved for ring shaped probe heads 1, since the dimensions are equal.

The probe opening D and suction displacement H can be selected to appropriately fit each specific application and materials. Typical ranges, in mm, are $1<D<20$ and $1<H<10$, with $D>=H$.

Figure 14B:
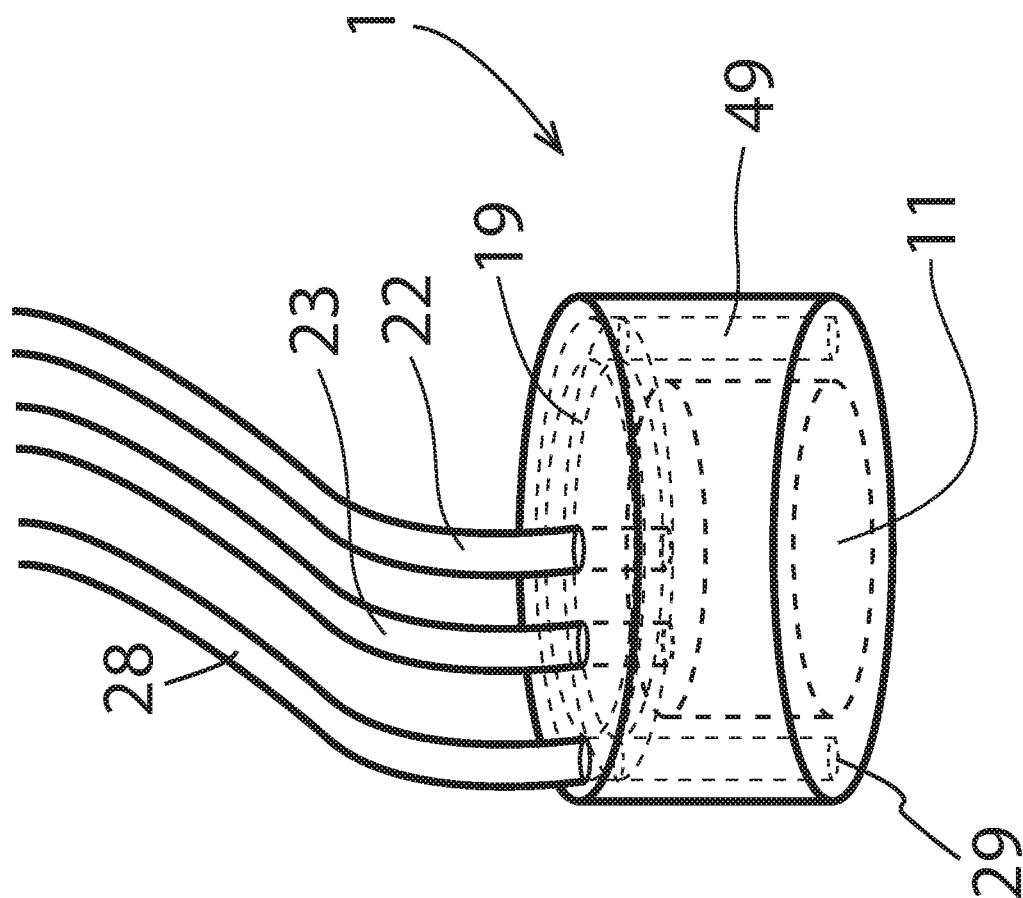
FIGS. 14A & 14B show a cross-sectional side view and a partially cross section perspective view of aspiration probe head with bottom surface or rim openings for enhanced adhesion to the tissue.
Figure 14A:
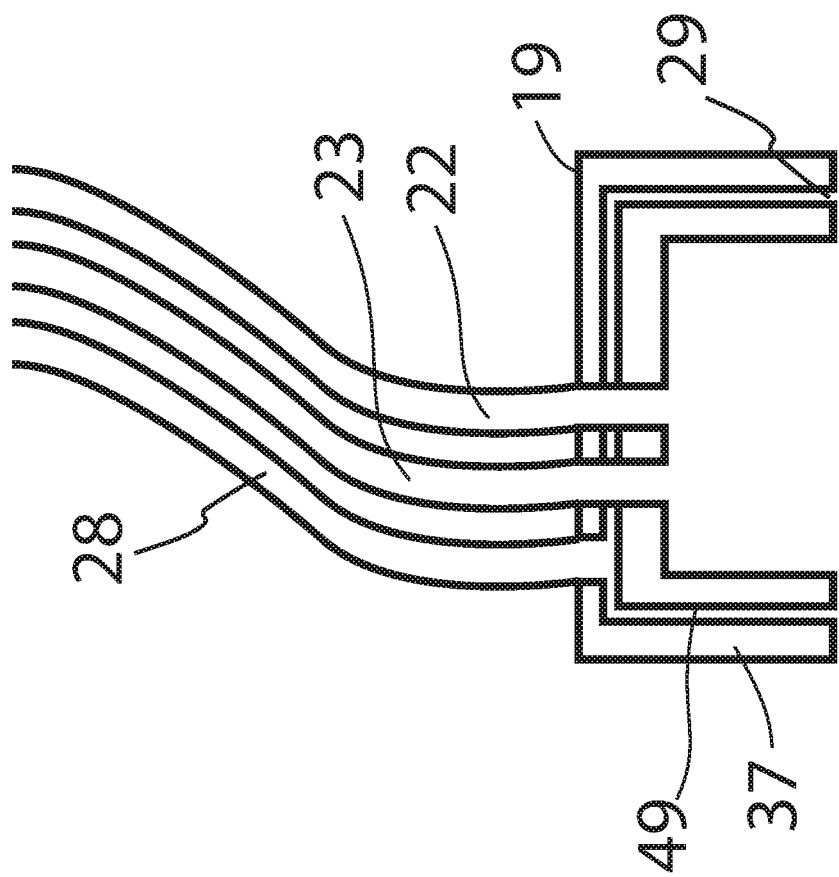

FIG. 14A shows a cross-sectional side view and FIG. 14B shows a partially cross section perspective view of aspiration probe head 1 with bottom surface or rim openings 29 for enhanced adhesion to the tissue 16 (vacuum clamping). The probe head 1 can include additional apertures 29 along the bottom surface 15, connected to a third airway 28, in order to enhance the adhesion of the probe head 1 by using suction on such apertures 29. FIG. 14B shows two apertures 29 at diametrically opposite part of the probe head walls. Of course, there can be more apertures, as 4, 6, 8 etc. which are equally angularly spaced, 90, 60 and 45 degrees between two apertures 29, wherein the connection to tube 28 is provided in the walls of the probe head 1.

In order to apply the probe head 1 inside a body cavity or opening, as to reach an internal surface, such as the uterine cervix, an optimized probe handle with an applicator or sleeve 30 is used as one exemplified in a perspective view of the device 101 according to FIG. 2.

Such probe device 101 consists of a hollow holding element or sleeve 30 that allows the user to position the probe head 1 at a remote location. This holding element 30 is hollow, containing the passage for the two airway tubings 2. The tubings 2 will pass without impediment through the holder, allowing the probe head 1 to freely detach from the holder 30, when the probe head 1 is sealingly connected to the tissue 16 and the user pulls the holding element 30 back. This simple embodiment does not have a contact force dampening functionality, however still allows for remote application of the tip, with subsequent detachment.

FIG. 3 shows a perspective view of the device 100 according to FIG. 1 inside a double sleeve applicator providing device 102. The probe head 1 can be in all embodiments being provided as shown e.g. FIG. 12, 13 or 14. The holding element according to device 102 comprises two concentric cylinders 31 and 131 having tuned friction. This is defined in a way that, when initially the inner cylinder 131 is pushed all the way to the tip side through holding the outer cylinder 31 the friction between the two cylinders maintains the element as a unit, although there is some withholding force through the tip (back surface 18 or 19 of the probe head 1) maintained against the front surface 231 of the inner sleeve 131. As the user puts in contact, the friction between sleeves 31 and 131 is sufficient to provide enough contact force, however, if the force is too large, it slides, preventing excessive force. The holding elements 31, 131 according to device 102 form a combined applicator sleeve that can then be pulled back as a unit in view of the friction between the two sleeves 31, 131 and the tip, i.e. the probe head 1, detaches.

FIG. 4 shows a further device according to FIG. 1 inside an alternative multi-sleeve applicator with an outer sleeve 32. This embodiment is also based on tuned friction, similarly to the embodiment FIG. 3. However, the inner cylinder comprises now two cylinders 36, each of them acting as airways as well. Therefore the outer cylinder sleeve 32 has two parallel through bores 132 to accommodate the rigid airways cylinders 36. The tuned friction is high enough to allow the tip or probe head 1 to be placed at the intended location, and to prevent excessive force as in FIG. 3. The particularity here is that, when the probe head 1 becomes connected to the tissue, the friction is low enough to allow free linear movement of the holder and outer sleeve 32 along the inner airways 36, and angular freedom is obtained by the flexible tubing 2 in the front of the rigid cylinders 36. It is to be pointed out that the length of the rigid tubes 36 is longer than the length of the sleeve 32 in order to allow this advance and retreating action, The difference in length can be e.g. between 3 and 7 cm. For friction tuning, a combination of low friction materials and geometric constraints can be used. Material mixes could be, for example, PEEK/PEEK or PEEK/fluoropolymer (e.g. fluorinated ethylene propylene (FEP) or polytetrafluoroethylene (PTFE)). A geometric realization would see an air gap between 36 and 132 of 0.05 to 0.3 mm, preferably 0.2 mm, for inner tubes 36 of outer diameter of 1.8 mm and bores of diameter 2.0 mm.

FIG. 5 shows a perspective view of a device according to FIG. 2 with a modified applicator with dampening element 7. In order to provide an improved connection of the probe head 1 with the sleeve 30, a contact force dampening element 7 using a high-compliance elastomer as a "bumper" for the applicator sleeve 30 is attached at the front side of the sleeve 30. Thus variations of the movement of the sleeve 30 with attached probe head 1 and the instant of the contact applies less contact force onto the tissue.

FIG. 6 shows a perspective view of the device according to FIG. 2 with a modified applicator 30 with a bellows bumper 8. The solution according to FIG. 8 is similar to the solution provided in FIG. 5 with a variation of contact force dampening, wherein a compressible bellows is attached at the front end of the sleeve 30.

FIG. 7 shows a perspective view of a device similar to FIG. 3 with a coil spring 9 based damper. Here an inner cylinder 20 is provided and introduced from the front end side of the sleeve 33 over the tubes 2, similar to the embodiment of FIG. 3. However, unlike to FIG. 3, this inner cylinder 20 is supported by an elastic spring 9. This spring 9 abuts on one side against the inner edge of the inner cylinder 20 and on the other side an inner abutment is provided within sleeve 33, e.g. through an inner shoulder, reducing the inner diameter of the sleeve providing an abutment surface for the spring 9.

Figure 8:
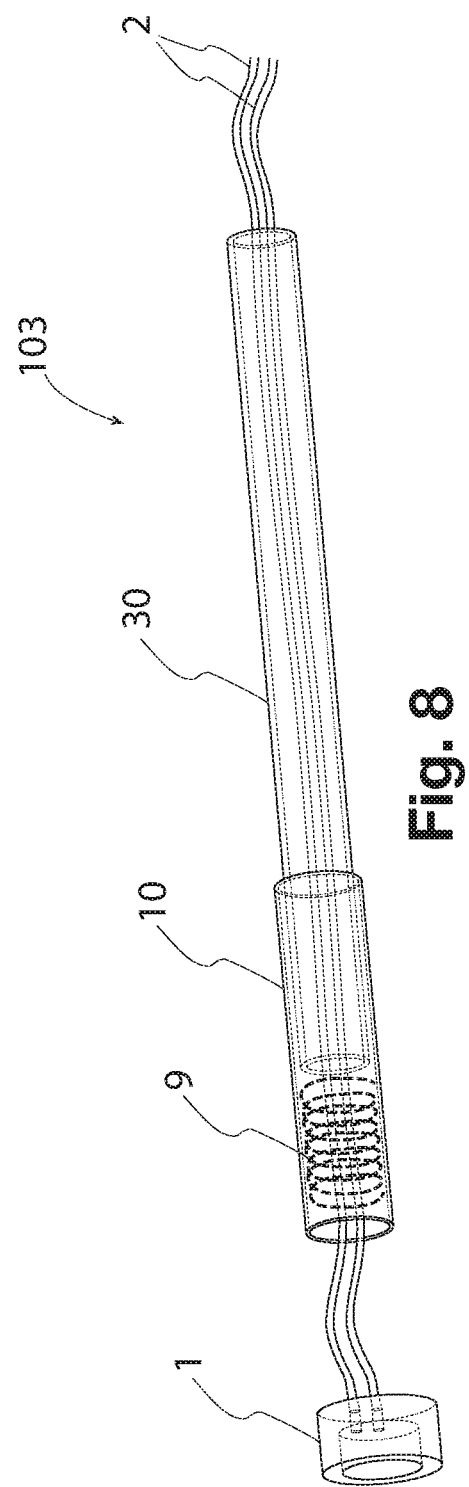
FIG. 8 shows a perspective view of a device similar to FIG. 7 with an alternative coil based damper.

FIG. 8 shows a perspective view of a device similar to FIG. 7 with an alternative coil 9 based damper. It comprises a spring-loaded moving component as an outer cylinder or sheath 10 as opposed to an inner cylinder 20. While essentially identical to FIG. 7, functionality wise this allows to print a scale bar on the holder sleeve 30, which is covered by the moving sheath 10, allowing the user to have informative feedback, and thus better sense of how much force he is applying. The outer cylinder 10 comprises, near its front end, an inner shoulder, reducing the inner diameter of the sheath providing an abutment surface for the spring 9.

FIGS. 9A, 9B & 9C shows perspective views of a device according to FIG. 8 in different use positions. The holding element according to device 103 may contain other mechanical elements, such as hollow tube 10 mounted on a spring 9, that allows the user to create sealing contact between the probe head 1 and the tissue 106, with minimal force interaction. In fact, a minimal amount of force might be initially needed, and the spring-loaded sliding tube 10 provides a means to minimize the force applied by the user, while allowing ample displacement that precludes the necessity of precisely controlled movements by the user. Alternatively, instead of a highly compliant spring 9, an elastomer, an elastic membrane or tuned friction between the moving components can provide similar ways of delivering the probe head 1 in a way that dampens or limits the maximum compressive forces. Such probe could also be mounted in an automated system for process control of synthetic materials.

FIG. 9A shows the starting position, wherein the upper surface 19 of the probe head 1 is maintained through slight pulling on tubes 22 and 23 against the front edge 110 surface of the device 103. The vacuum pumping device is running. Then the user pushes the device 103 forward in direction of the surface to be tested and the moment after the initial contact is shown in FIG. 9B. The spring 9 is compressed while slight pressure is created on the tissue. It is noted that the probe head 1 weighs less than 2 grams. FIG. 9C then shows the next step being the detached position. The probe head tip 1 is still in contact with the tissue (not shown). But the user is decoupling the probe head 1 through back pulling the sleeve 30; the spring 9 initially expands and the sheath 10 is pulled back as well. The probe head 1 remains connected only via the tubes 22 and 23.

Figure 11:
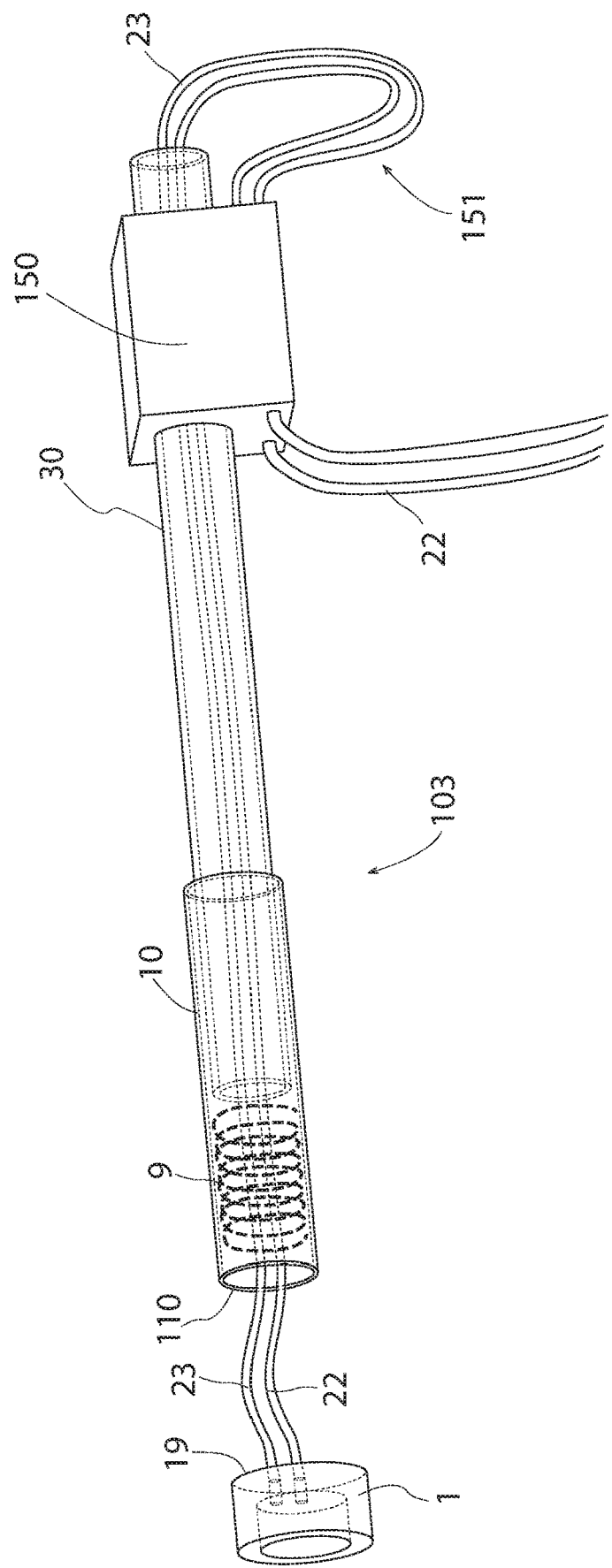
FIG. 11 shows a device which can be used inter alia in connection with the measurement of FIG. 10.

An example of usage of the probe to measure the mechanical properties of a biological tissue 106 inside a body cavity, such as the uterine cervix, is depicted in FIG. 10. The device 33 used as shown in FIG. 10 is the device 33 of FIG. 7. A method to use this probe in a remote tissue, using the probe handle is exemplified in FIG. 11. The device 103 used as shown in FIG. 11 is the device 103 of FIG. 8. Here the tubes 22 and 23 are passed through unit 150 providing a loop 151 of the tubes 22 and 23 leaving the proximal end of the sleeve 30. Unit 150 is used to "clip" and fix the air tubes to the probe, immobilizing them, thus preventing the weight of eventual long tubes to be transmitted directly to the probe head 1. The weight of the cables is supported by 30, and the probe head 1 is not subject to pulling forces, during probe retraction, except the friction on the tube 30. Loop 151 is the extra tube slack, necessary for the tip head detachment and tube extension. This acknowledges that the various features provided additional to sleeve and probe holder 30 can be exchanged obtaining similar results. With the probe head 1 placed near the examination region 140, the pump is turned on to allow suction to occur. The probe is moved by the user 40 forward towards the tissue, until contact is made and can be visually detected. Sealing of the probe head 1 by the tissue 216 can be detected by the increase in the negative pressure within the probe, e.g. with an audio signal being emitted when a negative pressure threshold is detected. If initial contact does not provide a seal, the user 40 can further push the probe handle inwards, in order to gently increase the contact force which results in a position of the sleeve in view of the probe head 1 as shown in FIG. 9B. Once the audio signal is emitted, the user stops this forward pushing movement. After another threshold pressure, at a greater negative value, is reached, the user receives a second audio signal instructing to pull the probe handle backwards. This threshold is determined so that the negative pressure is such that a retraction of the probe handle does not cause the probe head to fall off of the tissue due to too weak a vacuum level. After the probe handle is retracted, the measurement procedure is executed, with the displacement of the tissue closing the inner suction pipe 22 and the subsequent detection of a pressure difference by the sensors between pipes 22 and 23. If the negative holding pressure threshold is deemed low, the two threshold values can be combined into only one.

Figure 15:
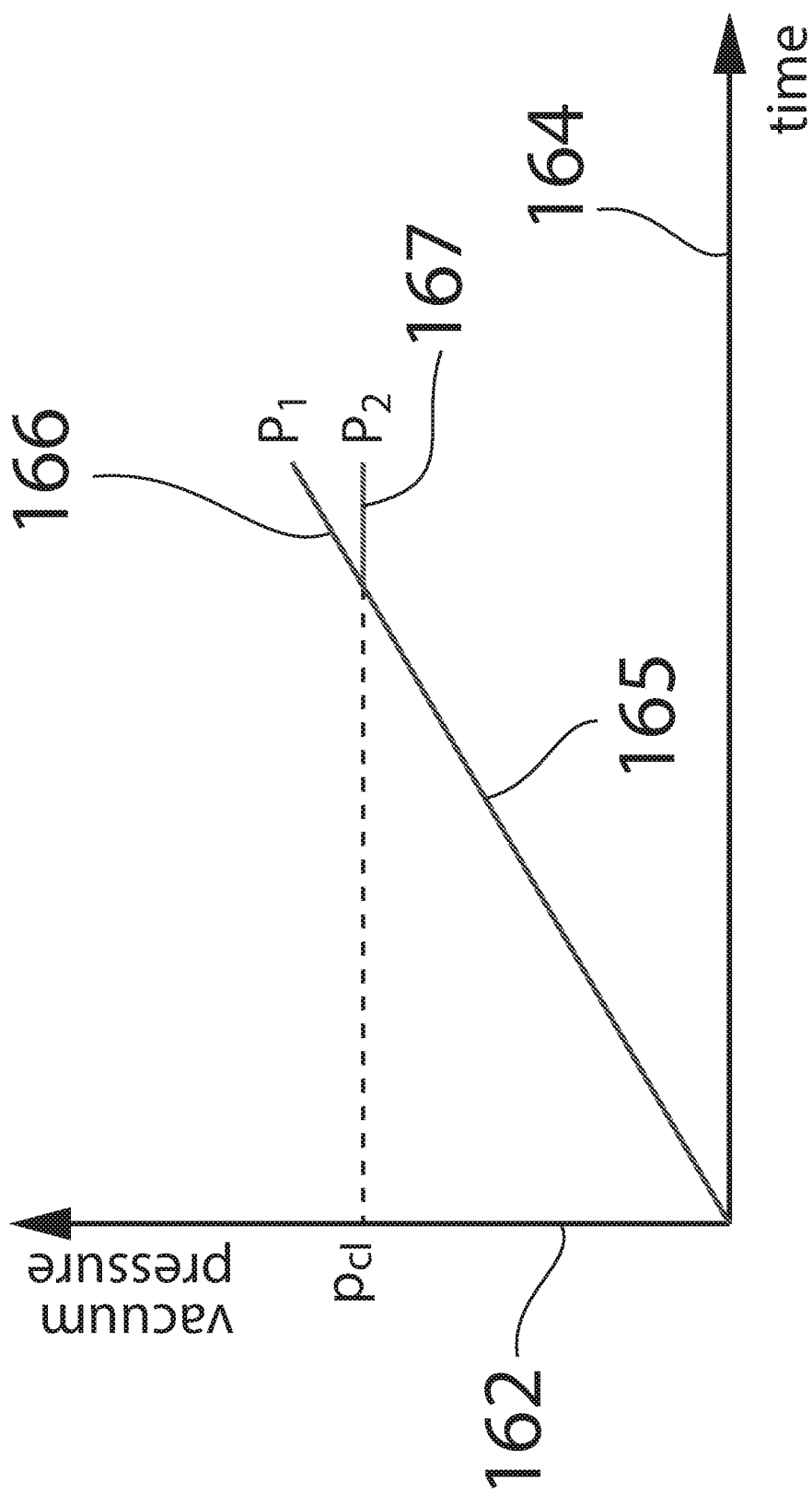
FIG. 15 shows a typical pressure versus time plot.
Figure 16:
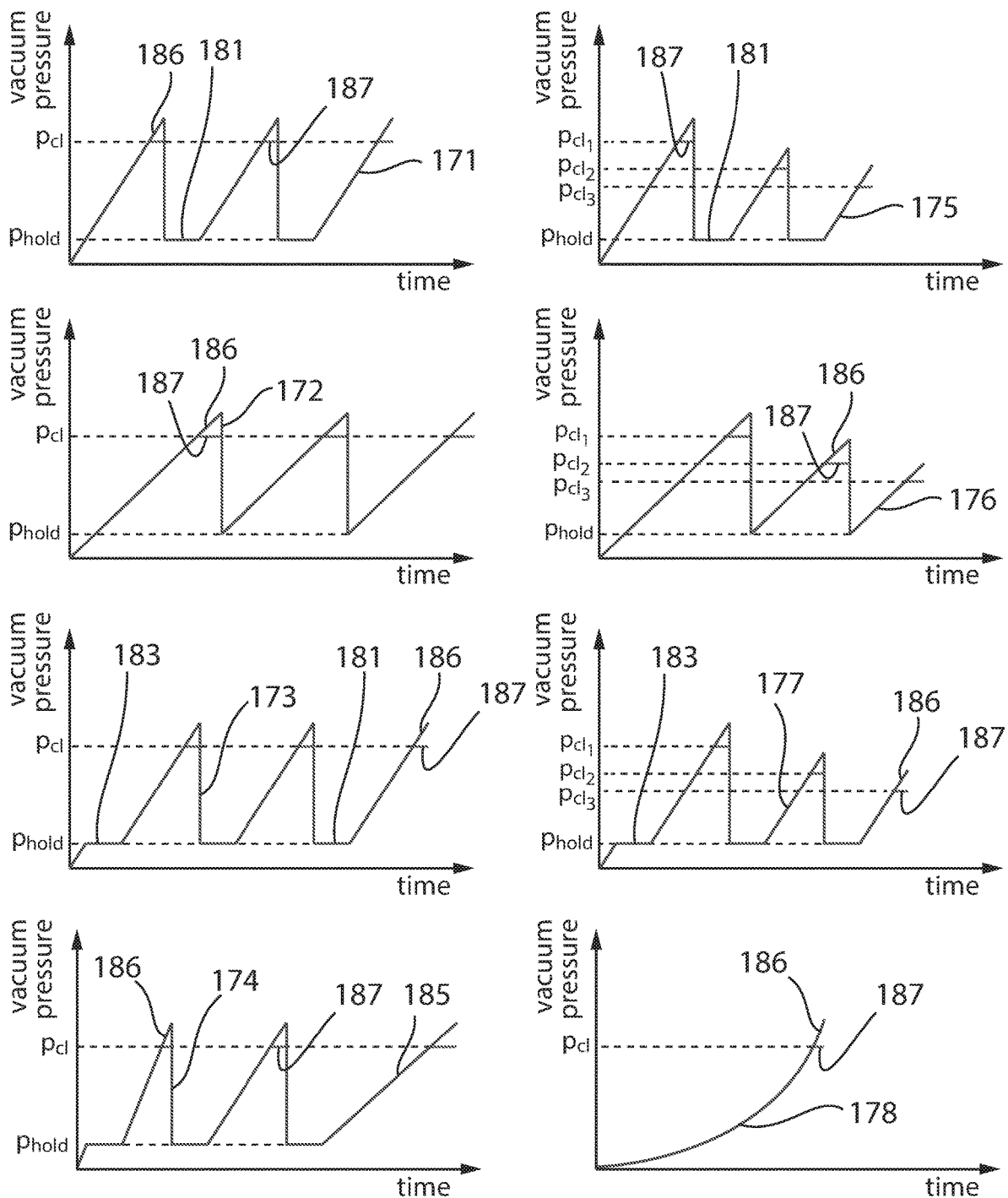
FIGS. 16A-16H show alternative types of pressure versus time profiles for investigating tissue viscoelastic properties, based on sequential measurements of similar or different aspiration rates.

FIG. 15 shows a typical pressure 162 versus time 164 plot 165, showing the increase in vacuum pressure inside the cavity, as measured by the two sensors P1 and P2. The moment when the tissue sealingly closes, the airway 22 connected to the pump and sensor P1 leads to a differential in pressure values between P1, that continues to increase and P2, measured through airway 23 that remains constant. In other words, there is a common plot portion 165, where the sensors connected to airways 22 and 23, P1 and P2 respectively, sense the same pressure P1=P2. Upon closure of the airway 22 as shown in FIG. 12B the two plots separate into an increasing negative pressure in plot 166 as measured by P1 for airway 22 and a constant negative pressure in plot 167 as measured by P2 for airway 23.

FIGS. 16A-16H show alternative types of pressure versus time profiles for investigating tissue viscoelastic properties, based on sequential measurements of similar or different aspiration rates, with variable periods of relaxation between measurements, or with non-linear pressure history.

The measurement can be used to determine relative differences in mechanical properties among materials of unknown viscoelastic properties, as well as in comparison to samples of known viscoelastic properties, by means of prior calibration steps. Typical pressure versus time plot are obtained by using a device according to an embodiment as shown in FIGS. 8, 9 and 11 allowing for the determination of the negative pressure required to obtain the set displacement D, with a given aspiration rate. Thanks to the minimal influence of external forces, for the whole duration of the measurement (up to the required time period, i.e. seconds, minutes, or more), this device can be used to reliably characterize the time dependence and loading history dependence of the mechanical behaviour of the tested material. To this end, the device can be used to apply sequential displacement measurements under different air aspiration rates, or by allowing variable relaxation intervals between aspiration measurements. In order to minimize potential uncertainties or variability due to probe repositioning and also to increase ease of usage in inaccessible locations, sequential measurements can be done, without entirely removing the vacuum pressure, but lowering it until a set holding pressure that allows the probe head to remain attached to the tissue. Several examples of sequential measurements are described in FIG. 9. The maintenance of the position of the probe head between aspirations, with minimized external forces thanks to the light weight of the probe, and the accurate determination of the closing pressure allowed by the differential measurement of the pressure sensors, can provide a reliable description of the underlying viscoelastic properties of the sample tissues, such as the response to creep or tissue relaxation. Specific loading protocols and corresponding output parameters can be defined for this purpose.

Plot 171 of FIG. 16A relates to a sequence of identical suction cycles going beyond the underpressure necessary for closure $p_{cl}$, with intermediate times 181 of a small holding underpressure value $p_{hold}$. As in FIG. 15, the plot 171 is of two curves that only separate at Pcl (diverging as portions 166 for P1 and 167 for P2 in FIG. 15). Therefore, when the vacuum pressure reaches Pcl, then the negative pressure increases in plot portion 186 showing the value of P1 for the airway 22 connected to the pump and closed at opening 14, wherein it stays stable in plot portion 187 at the value Pcl for the airway 23 connected to the cavity 11. The two plot portions 186 and 187 recombine, when the pump action stops and plot portion 186 reflects this by a dropping negative pressure "under" Pcl, when the closure of the cavity 11 at opening 14 is lifted and both airways 22 and 23 are open again which is reflected in the drawing that the two plot portions show no difference in the pressure valued at P1 and P2 in combined plot line 171.

Plot 172 relates to a sequence of identical suction cycles going beyond the underpressure necessary for closure $p_{cl}$, with a fallback to the small holding underpressure value $p_{hold}$, but starting over the next suction cycle. The pressure loss is less pronounced than in plot 171, e.g. the pump is working on a lesser suction level. The difference plot portions have received the identical reference numerals 186 and 187 in FIGS. 16A-16H.

Plot 173 is similar to plot 171, whereas a first plateau of initial holding time 183 at $p_{hold}$ before starting the sequence of identical suction cycles going beyond the underpressure necessary for closure $p_{cl}$, with intermediate times of a small holding underpressure value $p_{hold}$.

Plot 174 is similar to plot 173, whereas the suction cycles become longer with every cycle, i.e. the pump is slowed down to have a longer time before $p_{cl}$ is reached.

Plot 175 of FIG. 16B relates to a sequence of suction cycles with lowered amplitude, since the closing pressure $p_{cl1}$, $p_{cl2}$, $p_{cl3}$ decreases for every subsequent cycle which means that the deformed tissue 116 has a non-elastic behavior, although there are prolonged holding times 181.

Plot 176 shows a sequence similar to the result of plot 175, while there are no holding times 181 between suctions cycles.

Plot 177 is similar to plot 175 with an initial contact step 181, where after an initial increase of the suction negative pressure, the holding negative pressure $p_{hold}$ is maintained when the contact initially reached has been detected by the system.

Plot 178 shows one single cycle with an exponentially growing negative pressure until the closing pressure $p_{cl}$ is reached.

An advantageous realization of the interface between the probe head 1 and the probe handle 30, 31, 32, 33 etc., is by using an orientable probe head coupling on the handle. Such coupling can be used to allow the probe head to swivel, providing adaptation to the shape of the tissue surface without the need for probe handle angular adjustment. This can be achieved especially with a rounded dome 18 as described in FIG. 13C. Then a hollow sleeve like front edge 110 of any sleeve 20, 30, 31, 32, 33, including the front ends of elastomer 7 and bellows 8 allows having an oriented probe head 1. The direction of the probe head 1 can either be defined when the lower surface bottom edge 15 of the probe head 1 touches the tissue 16 or it can be predefined through pulling on the tubes 22 and 23 as for Bowden cables, since at least one is provided outside the center of the dome shaped 18 back side of the probe head 1.

The invention claimed is:

1. An aspiration device for measuring viscoelastic deformability of biological tissues and synthetic materials, the device comprising:
   a probe head having a form of a cup with a cavity, side walls and a bottom wall,
   a first probe channel,
   a pressure unit and a control unit, the first probe channel being configured to connect the pressure unit, that provides a vacuum inside first probe channel and that is controlled by the control unit, with the probe head,
   wherein the first probe channel has a distal end leading through the bottom wall into the cavity,
   wherein a second probe channel has a distal end leading through the bottom wall into the cavity and wherein the second probe channel is connected with a pressure sensor provided to determine a pressure in the cavity and to communicate the pressure to the control unit to determine a point in time when deformed biological tissue or synthetic material closes the distal end of the first probe channel based on a pressure difference between the first probe channel and the second probe channel.

2. The device according to claim 1, wherein the first probe channel and the second probe channel are flexible tubes passing loosely through a hollow sleeve allowing an essentially free relative movement between the probe head and the hollow sleeve.

3. The device according to claim 2, wherein a front edge of the hollow sleeve is configured to support the bottom wall of the probe head, thereby enabling a user to move the probe head and the sleeve as a single unit.

4. The device according to claim 3, wherein the bottom wall of the probe head has a rounded proximal outer surface to orient a longitudinal axis of the probe head not parallel to ea longitudinal axis of the hollow sleeve.

5. The device according to claim 4, wherein the loosely inserted flexible tubes are usable as Bowden cables to provide an orientation of the longitudinal axis of the probe head towards the longitudinal axis of the hollow sleeve.

6. The device according to claim 2, wherein a dampening element is fixedly attached at the front edge of the sleeve.

7. The device according to claim 2, wherein a bush is provided encompassing or inserted into the hollow sleeve, wherein an inner diameter of an outer of the bush or the hollow sleeve and an outer diameter of an inner of the hollow sleeve or the bush is chosen to accommodate the bush and the hollow sleeve within each other under a frictional contact.

8. The device according to claim 6, wherein the dampening element comprises a combination of a bush and a spring, wherein the spring is fixedly attached or abuts against an end wall of one of the hollow sleeve and the bush and is fixedly attached or abuts against a complementary connected shoulder of the other of the bush and the hollow sleeve.

9. The device according to claim 1, wherein the cavity has a volume measured up to a front surface between 0.78 microliter and 4 milliliter.

10. The device according to claim 9, wherein dimensions of a diameter or a length and a width, respectively, and a height are predetermined such that an aspect ratio of the probe head is between 1/4 and 2.

11. The device according to claim 9, wherein a thickness of the side walls of the probe head is between 0.3 and 2 millimeter, wherein the probe head is made of a plastic material, and wherein a weight of the probe head is less than 2 grams.

12. The device according to claim 1, wherein the probe head is shaped as a hollow cylinder having a closed internal cavity and comprises at least one recess at a distal end, the at least one recess being in connection to the pressure unit via a third probe channel, wherein the at least one recess is provided on an inclined wall portion of the inner side of the probe head.

13. The device according to claim 1, wherein the pressure unit is configured to provide a negative pressure of at least 100 mbar (75 mmHg).

14. A method for measuring viscoelastic deformability of biological tissues and synthetic materials by applying a vacuum on the biological tissue or synthetic material with a probe head according to claim 2, the method comprising:
   placing the probe head in an initial position on a front edge of the hollow sleeve;
   moving the hollow sleeve and the probe head, loosely connected via tubes or positioned on the front edge of the hollow sleeve;
   applying vacuum at least before contact of the probe head with the tissue or synthetic material is made;
   displacing the hollow sleeve along a longitudinal direction until a distal end of the probe head contacts the tissue or synthetic material and a holding vacuum is reached in the cavity;
   retracting the hollow sleeve along the longitudinal direction, while continuing to apply the holding vacuum or increasing the vacuum monotonically;
   increasing the vacuum monotonically until a sensor unit detects a difference in pressure between the two tubes, signaling the closure of the distal end; and
   interrupting the vacuum once one distal end of the probe channel is closed, wherein a deformability of the biological tissue or synthetic material is measured as a pressure difference between the initial position and a final position.

15. The method according to claim 14, further comprising:
   reducing the vacuum to a value at or larger than the holding vacuum,
   applying said vacuum for a predetermined intermediate time;
   increasing the vacuum monotonically until a sensor unit detects a difference in pressure between the two tubes, signaling a renewed closure of a distal end; and
   interrupting the vacuum once one distal end of the probe channel is closed, wherein the deformability of the biological tissue or the synthetic material is measured as a pressure difference between the initial position and the final position, wherein subsequent cycles have a different rate of change of the vacuum by becoming slower, faster, or changing in a predetermined pattern.

16. The device according to claim 1, wherein the distal end of the first probe channel extends at least partly into the cavity of the probe head.

17. The device according to claim 6, wherein the dampening element is a hollow elastomer or a bellows.

* * * * *